United States Patent [19]

Zelman

[11] Patent Number: 4,920,105

[45] Date of Patent: Apr. 24, 1990

[54] MEMBRANE POUCH

[75] Inventor: Allen Zelman, Vienna, Va.

[73] Assignee: Rensselaer Polytechnic Insitute, Troy, N.Y.

[21] Appl. No.: 71,666

[22] Filed: Jul. 9, 1987

[51] Int. Cl.⁵ ............................................. A61J 1/00
[52] U.S. Cl. ..................................... 514/59; 210/642; 210/647; 446/220; 446/221; 446/226; 604/56
[58] Field of Search ................... 514/59; 446/220, 221, 446/226; 210/642, 647; 604/56

[56] References Cited

U.S. PATENT DOCUMENTS

| | | | |
|---|---|---|---|
| 2,540,403 | 2/1951 | Meyers | 446/221 |
| 2,625,770 | 1/1953 | Steen et al. | 446/221 |
| 2,635,387 | 4/1953 | Anderson | 446/221 |
| 3,062,737 | 11/1962 | Azorlosa et al. | 210/644 |
| 3,702,820 | 11/1972 | Hough | 426/392 |
| 3,858,499 | 1/1975 | Scott | 99/495 |
| 4,142,966 | 3/1979 | Perry | 210/642 |
| 4,144,834 | 3/1979 | Donegan | 161/219 |
| 4,183,422 | 1/1980 | Williams | 446/220 |
| 4,306,556 | 11/1981 | Zelman | 128/272 |
| 4,396,383 | 8/1983 | Hart | 604/56 |
| 4,464,337 | 8/1984 | Zelman | 435/2 |
| 4,511,352 | 4/1985 | Theeuwes et al. | 604/56 |
| 4,552,555 | 11/1985 | Theeuwes | 604/56 |
| 4,767,544 | 8/1988 | Hamblin | 210/767 |

FOREIGN PATENT DOCUMENTS

| | | | |
|---|---|---|---|
| 121099 | 10/1984 | European Pat. Off. | 210/642 |
| WO83/03539 | 10/1983 | World Int. Prop. O. | 604/56 |

Primary Examiner—Ronald W. Griffin
Attorney, Agent, or Firm—Heslin & Rothenberg

[57] ABSTRACT

A membrane pouch, for rehydrating sterile intravenous and other solutions for non-sterilized fresh water, has a double bag construction. An inner bag made of semipermeable membrane material holds the sterile solutes to be rehydrated. The membrane material is permeable by water but impermeable to contaminants and a large molecular weight solute contained in the bag. An outer waterproof bag encloses the membrane bag and serves as a container for fresh water. Each bag has a sealable valve for providing access to the interior thereof. A high molecular weight dye located in the outer bag provides a visible indication of the existence of any discontinuity in the membrane bag. A low molecular weight, water soluble, non-toxic substance having a high osmotic pressure can be placed inside the membrane bag to accelerate the osmotic transfer of sterile water from the outer bag into the inner membrane bag.

24 Claims, 3 Drawing Sheets

MEMBRANE POUCH

Government Rights

This invention was made with Government support under Contract No. NOOO 14-82-K-0614 awarded by the U.S. Navy. The government has certain rights in this invention.

BACKGROUND OF THE INVENTION

1. Technical Field

This invention relates generally to rehydration of dehydrated solutions and more particularly to a method and structure for producing a sterile solution by hydrating a solute via osmosis through a semipermeable membrane from non-sterilized fresh water. The invention is particularly useful for rehydrating pharmaceuticals and intravenous solutions.

2. Background Art

At locations remote from supplies of clean water and sterilization facilities, it is often extremely difficult to obtain uncontaminated aqueous solutions suitable for ingestion or injection. Typically, one needs to transport sterile solutions themselves or both a sterile solute and sterile water in bottles or other containers to such remote locations. Bottles and other similar containers are generally large, heavy and bulky to carry resulting in either substantial shipping costs or the limited availability of such solutions at isolated locations.

For intravenous injections, it is known that an aqueous solution of dextran and sodium chloride in the right proportions can be used as a plasma substitute. Bottles of such solutions are available, presterilized, from pharmaceutical companies but are difficult to obtain at, or transport to, remote locations in substantial quantities. The alternative of reconstituting such a solution from the dehydrated solute and sterile water (or sterile saline) presents similar difficulties.

Fresh water (i.e. non-seawater) is often available at remote locations but because of contaminants such as bacteria, viruses, pyrogens, silt and the like is generally unsuitable for use in rehydrating aqueous solutions. For drinking purposes, naturally occurring water can be sterilized by adding chemicals such as chlorine or iodine to it. However, this requires the transport of large quantities of such chemicals and, further, these chemicals have a tendency to make the water impalatable and sometimes indigestible. Such chemically treated water is totally unsuitable for use in rehydrating an intravenous solution since any bacteria, pyrogens or viruses, in the solution, although dead, would still cause havoc with the body's immune system.

A need thus exists for a means of simply and safely rehydrating a dehydrated pharmaceutical solution, such as an intravenous solution, from contaminated fresh water.

SUMMARY OF THE INVENTION

This need is satisfied, in accordance with the present invention, by the provision of a membrane pouch especially designed to facilitate rehydration of dehydrated pharmaceutical and other solutions from non-sterilized fresh water. The membrane pouch relies upon osmosis to rehydrate a solute and employs a semipermeable membrane member which is permeable to water but impermeable to contaminants and high molecular weight solute. The membrane member acts as an absolute barrier to bacteria, virus, pyrogens and other contaminants. A dye or other suitable means can be used with the pouch to visually indicate the existence of any discontinuity, e.g. perforation, in the membrane member.

The pouch preferably has a double-bag construction with the inner bag made of suitable semipermeable membrane material, preferably pleated, to maximize its surface area. An outer waterproof bag substantially encloses the inner bag and provides not only a convenient container for fresh water but also provides protection to the inner bag. A sealable port, of any suitable construction, is provided on each bag for ready access to the interior thereof. The second bag may be provided with a separable sealed extension for shielding the port of the inner bag. A dye having a molecular weight significantly greater than the molecular weight cut-off of the semipermeable membrane member may be placed in the space between the inner and outer bags as a fail-safe mechanism to provide a visible indication of a leak in the membrane member. In such an embodiment, both bags would be made at least partially transparent.

In an advantageous application of the invention, a large molecular weight osmotic agent to be rehydrated and an osmotic accelerator are placed inside the inner bag of the membrane pouch. The large molecular weight substance is impermeant to the membrane member and preferably has a relatively high osmotic pressure for its large molecular weight. The osmotic accelerator comprises a non-toxic, water soluble, low molecular weight substance which is permeant to the membrane member and possesses a high osmotic pressure. The large molecular weight substance can advantageously comprise a polysaccharide such as dextran or dextrin while the osmotic accelerator can be a sugar or mineral salt. Dextran and sodium chloride, for example, can be used to reconstitute an intravenous solution.

In operation, the solute to be rehydrated, e.g. a large molecular weight substance, and a suitable osmotic accelerator, in sterile condition, are located within the sealed inner bag composed of semipermeable membrane material. Unsterilized fresh water is placed in the outer bag external and adjacent to the membrane material of the inner bag, and the pouch is shaken. The osmotic accelerator serves to quickly draw sterile water into the inner bag and wet the large molecular weight substance. The osmotic accelerator diffuses out through the membrane material, dissolves in the water and reaches equilibrium at a particular desired concentration in the water inside both bags. The wet large molecular weight substance is locked inside the inner bag and due to its osmotic pressure draws water containing the dissolved osmotic accelerator into the inner bag. The concentration of the large molecular weight substance in the inner bag decreases with time until essentially all of the water is drawn into the inner bag.

Accordingly, a principle object of the invention is to provide a method and structure for rehydrating dehydrated solutions simply and safely from non-sterilized fresh water.

Another object is to provide apparatus for producing a sterile solution by rehydrating a solute from contaminated fresh water.

Another object is to provide a solution rehydration device which is lightweight, fail-safe, easy to transport and use, and can be readily and inexpensively manufactured.

Yet another object is to provide a membrane pouch in which sterile solute can be economically packaged, efficiently stored for long periods of time, easily transported and then rehydrated at remote locations, or for emergency purposes, without the necessity for sterilized water.

A further object is to provide a solution rehydration method and structure which is extremely versatile and can be used to produce various intravenous solutions, other pharmaceutical solutions, comestible solutions and the like, from muddy, swamp, brackish or otherwise contaminated fresh water.

A still further object is to provide a process and apparatus for rehydrating dehydrated solutions which eliminates the need for obtaining, transporting, storing and using previously sterilized water.

Another object is to provide a structure and process for controllably and rapidly producing desired sterile aqueous solutions.

BRIEF DESCRIPTION OF THE DRAWINGS

These and other objects, advantages and features of the present invention will be more fully understood from the following detailed description when read in conjunction with the accompanying drawings in which.

DETAILED DESCRIPTION

Figure 1:
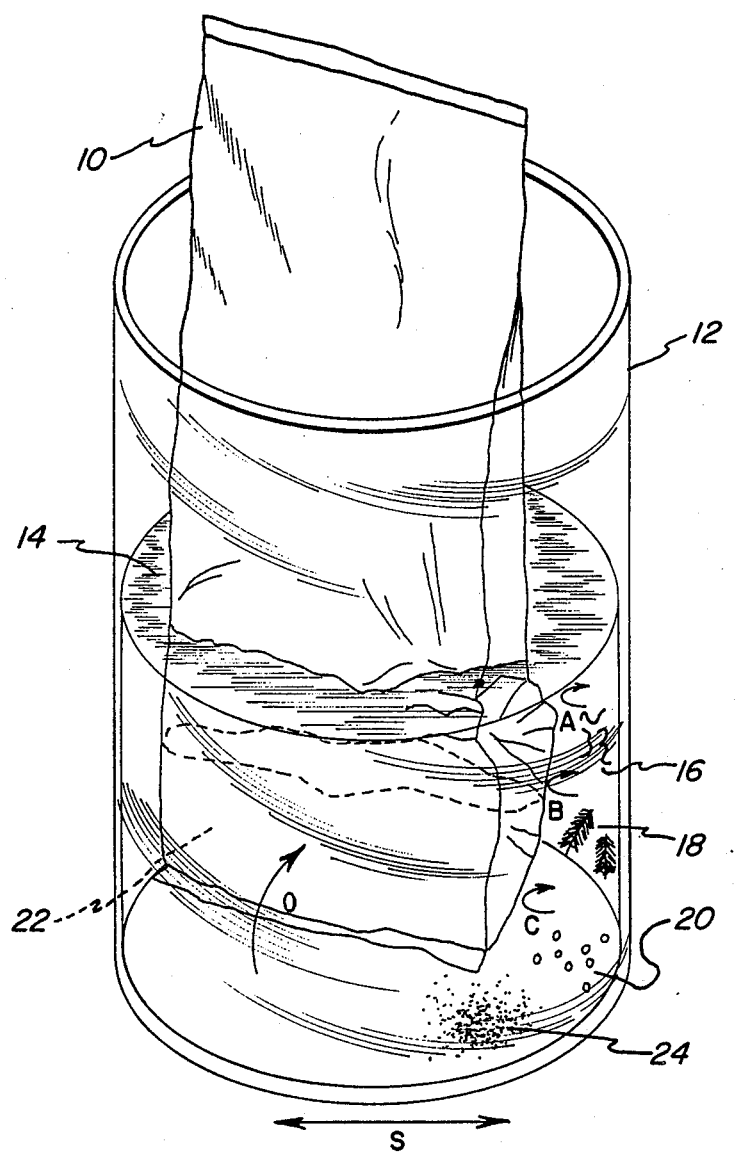
FIG. 1 depicts the basic operation and characteristics of a semipermeable membrane bag.

FIG. 1 is instructive in understanding the general operating principles of the present invention. As shown therein, a bag 10 made of semipermeable membrane material is located in a container 12 which can be filled with non-sterilized fresh water 14 containing contaminants such as viruses 16, bacteria 18 and pyrogens 20. The semipermeable membrane material from which bag 10 is constructed has a molecular weight cutoff which makes the bag impermeable to the contaminants in water 14, as schematically illustrated by arrows A, B and C. The bag is permeable to water molecules which can be drawn into the bag by osmosis, as indicated by arrow 0.

Contained within bag 10 is a suitable quantity of sterile solute which is to be rehydrated. The nature of the solute can vary widely depending upon the aqueous solution desired. The solute may take a dry powdered form or any other concentrated form.

The interior of membrane bag 10 and the solute 22 placed therein are sterilized, either before loading of the solute or in situ. The bag is then sealed to maintain the sterility of its contents. The bag can advantageously be constructed of a clear plastic, polycarbonate based membrane material which is heat sealable, although other equivalent materials (e.g. most materials used for hemodialysis) and other sealing techniques (e.g. gluing) may also be employed.

To ensure that the membrane material of bag 10 is intact, i.e. contains no perforations or other discontinuities, a small quantity of dye 24 having a molecular weight significantly higher than (e.g. 10x) the molecular weight cutoff of bag 10 can be placed in water 14. The dye acts as a failsafe mechanism providing a visible indication, by its appearance within the interior of bag 10, of a breach in the continuity of the surface of the bag and therefore of the possibility of contamination of its contents. The dye indicator is a useful safety feature but is not an essential ingredient for the rehydration process to work. As an alternative to putting a high molecular weight dye in container 12 that will penetrate inside the bag through a perforation, a substance which is sensitive to contamination can be placed in the interior of bag 10. For instance, sodium nitrite causes bacteria to give off a pinkish color and if placed on the inside of bag 10 would provide a visible indication, i.e. a color change, upon contacting such contamination. Of course, other materials and/or arrangements having similar characteristics may also be used for this purpose.

In accordance with one particularly advantageous aspect of the present invention, the solute 22 includes a large molecular weight osmotic agent, and an osmotic accelerator. The large molecular weight osmotic agent can comprise a polysacchride or other substance having a molecular weight greater than the molecular weight cutoff of the membrane material and a large osmotic pressure. Dextran which is non-toxic when put directly into the bloodstream can be used for this purpose in rehydrating intravenous solutions. Dextrin can be used in rehydrating food products or drinks.

The osmotic accelerator generally comprises a low molecular weight, water soluble, non-toxic substance which is permeant to membrane bag 10 and exhibits a high osmotic pressure. The osmotic accelerator, as its name suggests, serves to initiate and accelerate the rehydration process. Depending upon the nature and use of the desired solution, mineral salts and/or sugars, or other substances with the described characteristics, can be used as the osmotic accelerator.

In operation, the osmotic accelerator serves to very rapidly draw water into membrane bag 10 thereby wetting and dissolving the large molecular weight substance. The osmotic accelerator because of its low molecular weight diffuses out through the membrane material and ends up equilibrating between the outside and the inside water. The large molecular weight substance dissolved in sterile water brought into the membrane bag by the osmotic accelerator now through its osmotic pressure draws additional sterile water into the bag. The osmotic accelerator which is dissolved at equilibrium throughout the water in the container flows back inside the bag with the osmotically drawn sterile water. The large molecular weight substance is locked inside the bag. The concentration of the osmotic accelerator remains at equilibrium while the concentration of the large molecular weight substance in aqueous solution inside the bag decreases with time until essentially all of the water originally in container 12 is inside the bag. The concentration in the rehydrated solution of the large molecular weight substance is thus a function of the time that the bag is emerged in water 14 and the concentration of the osmotic accelerator is a function of the quantity of water placed in container 12. To further accelerate the process, the container 12 can be agitated as symbolicly indicated by double headed arrow S.

Several embodiments of a membrane pouch specially designed to facilite the rehydration process of the present invention, will now be described.

Figure 2:
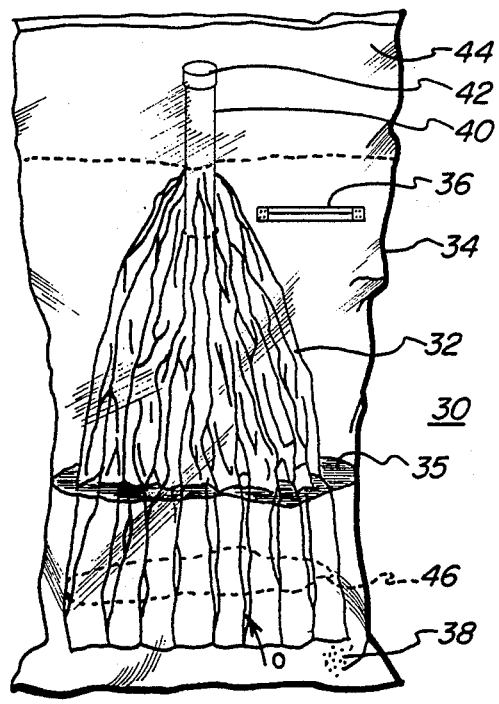
FIG. 2 illustrates a preferred form of the membrane pouch of the present invention.

In FIG. 2, a membrane pouch 30 particularly suitable for rehydrating intraveneous or other pharmaceutical solutions from non-sterilized fresh water is shown. Pouch 30 includes a closed inner bag 32 made of semipermeable membrane material. Bag 32 is preferably pleated to allow for volume expansion and to maximize surface area available for osmotic transfer. The bag is, preferably, at least in part, transparent, and is composed of any suitable semipermeable membrane member having a molecular weight cutoff which prevents penetration therethrough of viruses, bacteria, pyrogens and other contaminants. Generally, any membrane material suitable for hemodialysis can be used in this invention. In one implementation, a standard polycarbonate membrane member having a molecular weight cutoff of 20,000 daltons was used to construct the inner bag 32. This material has the advantage that it is readily heat sealable. Whatever membrane material is selected, it should have a molecular weight cutoff sufficient to block the passage therethrough of contaminants, the high molecular weight solute and a dye indicator, and be permeable to water and the osmotic accelerator. The membrane material of inner bag 32 is typically 10–20 microns thick.

To protect the thin membrane bag from mechanical stress and provide a container for the fresh water, an outer waterproof bag 34 substantially encloses the inner bag 32. This outer bag is preferably made of clear plastic material such as Lexan ® having a thickness on the order of 1–5 mils. Bag 34 is sized to contain a sufficient volume of water 35 for the particular intended rehydration application. The edges of bag 34 can be closed, e.g. by heat sealing, so as to completely enfold the inner bag 32. A zip-lock type valve 36, or other sealable valve, permits introduction of fresh water into the interior of bag 34 in the space surrounding membrane bag 32.

A dye indicator 38 such as a small quantity of 200,000 dalton blue dextran can be placed in the space between the inner and outer bags to provide a visible indication of any discontinuities in the membrane material. Other substances may of course be employed to provide a desired visible indication of a perforation in the membrane material and/or resulting potential contamination of the contents of the membrane bag.

In the embodiment of FIG. 2, the membrane bag 32 is provided with an injection port 40 consisting of an elongated hollow tube or straw, one end of which is secured to the membrane material and extends into the membrane bag 32, and the other end mounts an injection port cap 42. Cap 42 can be made of rubber or other suitable material penetrable by a hypodermic needle for extraction of the intravenous or pharmaceutical solution rehydrated in bag 32. Sealable port 40 may of course assume other configurations depending upon the intended application. Injection port shield 44 preferably comprising a sealed, separable extension of outer bag 34 encloses and protects the injection port 40.

Located inside membrane bag 32 are the sterile solutes 46 to be rehydrated. These preferably include a large molecular weight osmotic agent such as a polysaccharide and a low molecular weight osmotic accelerator such as a mineral salt or sugar. Dextran and NaCl can be used to produce a sterile intravenous isotonic solution from non-sterilized fresh water.

Experiments have been successfully conducted with such a membrane bag using tap water, swamp water, muddy water and other types of non-sterilized fresh water. Experiments employing tap water will now be described. Into a membrane bag (6"×10") was placed dextran in various molecular weights and amounts, plus 7.2 g NaCl. Each membrane bag was sealed inside a Lexan ® polycarbonate outer bag which was filled with 800 ml of water at 60° C. A pinch of 200,000 daltan blue dextran was placed in the outer bag. If the blue dextran penetrates the membrane material, then one knows that the membrane is not intact; thus the pouch is fail-safe. The pouch was shaken at 78 rpm and a constant temperature of 60° C. Within 15 minutes, the sodium chloride had equilibrated with all the water in the inner and outer bags producing 0.9 g/100 ml NaCl.

The NaCl is responsible for bringing into the membrane bag about 25 ml of water which dissolves the dextran. Dextran because of its high molecular weight is impermeant to the membrane bag and because of its relatively high osmotic pressure causes water to continue entering the inner bag until essentially all of the water is removed from the outer bag (in approximately 24 hours). The sodium chloride diffuses through the membrane material and reaches equilibrium throughout the water in the pouch (in the example given, at 0.9 g/100 ml). The concentration of dextran continues to decrease as water enters the membrane bag. Intravenous solution of 40,000 daltan dextran at 10 g/100 ml plus 0.9 g/100 ml NaCl are commonly used as volume expanders. The experimental data from the table below indicates that this solution can be produced from dehydrated dextran and NaCl and tap water in less than 2 hours with H₂O at 60° C. and with membrane pouch agitation at 78 rpm.

| | Producing a Sterile Intravenous Solution from Non-Sterile Water, Rehydratable Solutes and a Membrane Pouch ||||||
| | 2 hr. || 4 hr. || 6 hr. ||
| dextran | V ml | dextran $\frac{g}{100\ ml}$ | V ml | dextran $\frac{g}{100\ ml}$ | V ml | dextran $\frac{g}{100\ ml}$ |
| --- | --- | --- | --- | --- | --- | --- |
| 17,600 MW, 40 g | 402 | 9.95 | 557 | 7.18 | 605 | 6.61 |
| 17,600 MW, 60 g | | | | | 680 | 8.82 |
| 40,000 MW, 40 g | 450 | 8.89 | 595 | 6.72 | 685 | 5.84 |
| 76,800 MW, 40 g | 315 | 12.7 | 512 | 7.81 | 585 | 6.84 |
| 76,800 MW, 60 g | | | | | 705 | 8.51 |

All experiments with 800 ml H₂O in outside pouch, blue dextran in outer pouch to indicate bag leaks, 60° C., shaking at 78 rpm, and "standard" polycarbonate membrane used. In each pouch was 7.2 g NaCl plus the mass of dextran noted in the table. Final concentration of NaCl in all pouches was 0.9 g/100 ml.

Figure 3:
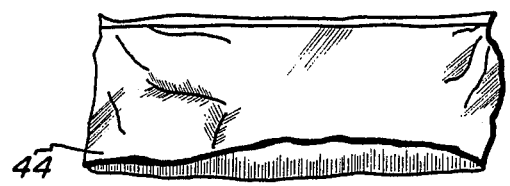
FIG. 3 depicts the membrane pouch of FIG. 2 after rehydration.
Figure 3:
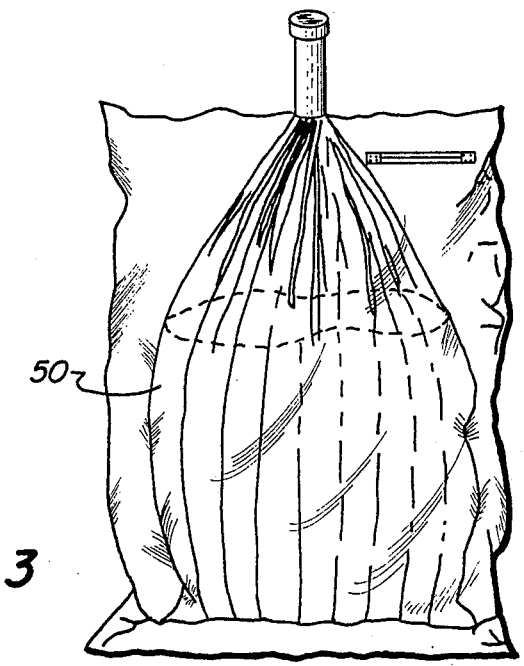

FIG. 3 illustrates the membrane pouch with the rehydrated intravenous solution 50 ready for injection and the injection port shield 44 removed.

The membrane pouch of the present invention can be used to reconstitute other intravenous solutions (e.g.

Factor VIII—a blood clotting component used to treat hemophyliacs), other pharmaceutical solutions, drinks (e.g. drinking water, Gatorade), other food products (e.g. meats, potatoes, chili con carne, beef bouillon) and other aqueous solutions. Dextran is preferred as the large molecular weight osmotic agent for intravenous and pharmaceutical solutions while dextrin is preferred for comestibles. In place of sodium chloride, calcium chloride, calcium carbonate, potassium chloride or other mineral salts, or glucose, sucrose or other sugars, or other equivalent substances, can be used as an osmotic accelerator depending upon the particular application. In some instances, the membrane pouch of the present invention can be successfully employed to rehydrate materials containing naturally occuring high molecular weight osmotic agents and/or osmotic accelerators. In certain circumstances, it may also be possible to advantageously use the membrane pouch without employing both the large molecular weight osmotic agent and an osmotic accelerator.

Figure 4:
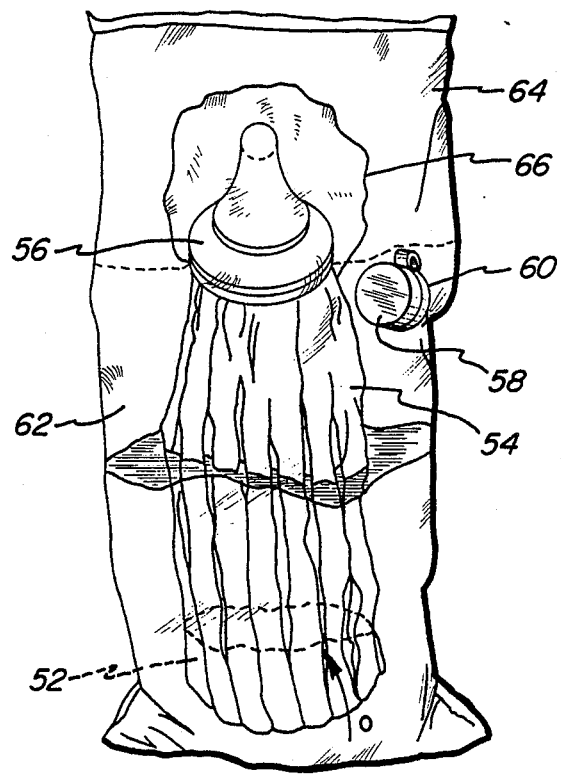
FIG. 4 depicts another embodiment of the membrane pouch, in the form of a baby bottle.

The design of the pouch can be tailored to the particular application. By way of example, the access port of the semipermeable membrane bag may take the form of a mouthpiece when rehydrating comestibles. FIG. 4 shows a membrane pouch for rehydrating powdered milk 52 wherein the inner bag 54 takes the 0 shape of a baby bottle with a nipple 56 as the access port. A tethered cap 58 serves as a sealing member for a valve 60 in the outer bag 62. In addition to a pull-off nipple shield 64, nipple 56 is sheathed in an optional sterile membrane cap 66.

Figure 5:
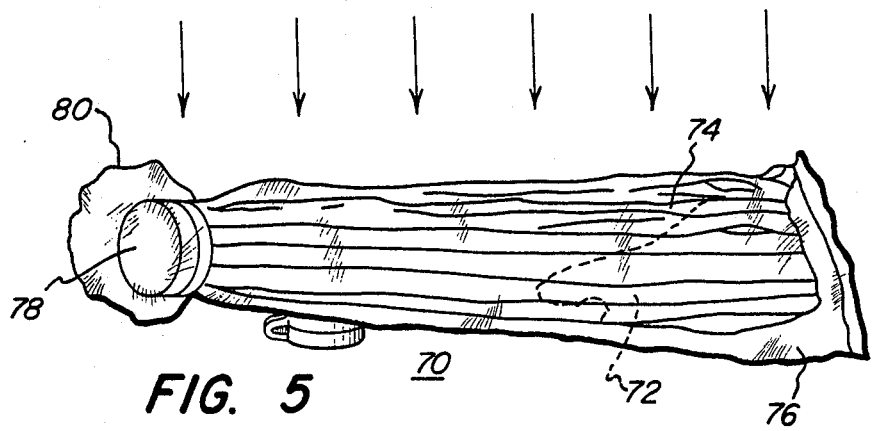
FIG. 5 illustrates yet another embodiment of the membrane pouch and in situ sterilization of the solute to be rehydrated.

To produce a sterile solution, the solute and interior of the inner membrane bag must be sterile. This can advantageously be accomplished, in situ, by gamma or electron sterilization as diagrammatically illustrated in FIG. 5. The membrane pouch 70, as shown in FIG. 5, with dry solute 72 in inner bag 74, thus sterilized and sealed within outer bag 76, and with its access cap 78 enclosed within a protective and/or sterile shield 80, can be easily stored and shipped for use with any readily available fresh water source. (Because of the membrane material's permeability to salts, seawater would not be suitable for use in the pouch).

It will thus be apparent that the membrane pouch of the present invention provides a simple, safe, economical structure for rapidly rehydrating sterile solutions from non-sterilized fresh water. The invention is capable of wide application and of beneficial use in numerous circumstances including remote locations, emergency situations, the aftermath of natural disasters, impoverished areas, etc. The invention clearly fulfills all of the objects set forth hereinbefore.

Although various embodiments of the invention have been depicted and described for illustrative purposes, it will be apparent to those skilled in the relevant art that various modifications, substitutions, additions and the like may be made without departing from the spirit of the invention, the scope of which is defined by the claims appended hereto.

What I claim is:

1. A membrane pouch for producing a sterile solution from non-sterilized fresh water, the pouch comprising:
   a first closed bag of semipermeable membrane material, said membrane material being permeable to water molecules and impermeable to viruses, bacteria and pyrogens;
   a second, waterproof bag substantially enclosing said first bag;
   first sealable port means for providing access to a first compartment within said first bag;
   second sealable port means for providing access to a second compartment, said second compartment lying between said first bag and said second bag; and
   a sterile solute to be hydrated located in one of said first and second compartments, said solute comprising a large molecular weight osmotic agent which is impermeant to said membrane material and an osmotic accelerator, said osmotic accelerator comprising a non-toxic, water soluble, low molecular weight substance which is permeant to said membrane member and possesses a high osmotic pressure, said accelerator serving to initiate and accelerate hydrating of the osmotic agent, whereby fresh water placed in the other of said compartments is transferred by accelerated osmosis to said one of said compartments containing said solute while the membrane material precludes passage of bacteria, viruses and pyrogens therethrough.

2. The pouch of claim 1 wherein said large molecular weight osmotic agent comprises a polysaccharide and said osmotic accelerator is selected from the group consisting of mineral salts and sugars.

3. The pouch of claim 2 wherein said osmotic agent comprises a first quantity of dextran and said osmotic accelerator comprises a second quantity of sodium chloride, and wherein said first and second quantities are such as to produce a usable intravenous solution when rehydrated with fresh water from said second compartment.

4. A membrane pouch especially suitable for producing a sterile solution from non-sterilized fresh water, the pouch comprising:
   a first closed bag of semipermeable membrane material, said membrane material being permeable to water molecules and impermeable to viruses, bacteria and pyrogens;
   a second, waterproof bag substantially enclosing said first bag;
   first sealable port means for providing access to a first compartment within said first bag, said first port means extending through said second bag;
   second sealable port means for providing access to a second compartment, said second compartment lying between said first bag and said second bag, whereby fresh water placed in one of said first and second compartments can be transferred by osmosis to the other of said compartments while the membrane material precludes passage of bacteria, viruses and pyrogens therethrough; and
   indicator means for providing an indication if the first bag is not intact, said first and second bags being at least partially transparent, said indicator means providing a color indication of the existence of a discontinuity in the first bag.

5. The pouch of claim 4 wherein said indicator means comprises a dye placed in one of said first and second compartments, said dye being selected to have a molecular weight greater than the molecular weight cut-off of the membrane material such that the dye does not pass through the membrane material unless said material contains a discontinuity.

6. The pouch of claim 5 wherein the first bag is pleated.

7. The pouch of claim 6 wherein a portion of said first port means extends beyond said second bag, and said pouch further comprises a shield surrounding said portion of said first port means.

8. The pouch of claim 7 wherein said shield comprises a separable sealed extension of said second bag.

9. The pouch of claim 8 wherein said first port means comprises a hollow tube, said tube having one end which extends into said first bag and a second end which is provided with a removable cap.

10. The pouch of claim 8 wherein said first port means comprises a mouthpiece.

11. The pouch of claim 4 further comprising a solute desired to be rehydrated located in said first compartment.

12. The pouch of claim 11 wherein said first compartment and said solute are sterile.

13. The pouch of claim 12 wherein said solute comprises dehydrated mil,.

14. The pouch of claim 12 wherein said solute comprises a dehydrated pharmaceutical.

15. The pouch of claim 4 further comprising a sterile solute in said first compartment, said solute comprising a large molecular weight osmotic agent.

16. Apparatus for producing a sterile solution by hydrating a solute from non-sterilized fresh water, comprising:
  first sealable container means for receiving said solute;
  second waterproof container means for receiving nonsterilized fresh water;
  a semipermeable membrane member common to said first and second container means, said membrane member being permeable to water molecules and impermeable to bacteria, pyrogens, viruses and said solute; and
  an osmotic accelerator initially located in said first container means, said osmotic accelerator comprising a water soluble, non-toxic substance having a high osmotic pressure and being permeant to said membrane member, and wherein the osmotic accelerator serves to initially draw a first quantity of water from said second container means into said first container means through said semipermeable membrane member to wet said solute and said accelerator equilibrates throughout the water in said first and second container means, and said wet solute, through osmosis, draws water containing said equilibrated accelerator into said first container means through said membrane member.

17. The apparatus of claim 16 wherein said solute comprises a polysaccharide and said osmotic accelerator comprises a substance selected from the group consisting of mineral salts and sugars.

18. The apparatus of claim 17 wherein said solute comprises a first quantity of dextran and said osmotic accelerator comprises a second quantity of sodium chloride, and wherein said first and second quantities are such as to produce a usable intravenous solution when rehydrated with water from said second compartment.

19. The apparatus of claim 16 further comprising a dye indicator located in said second container means, said dye indicator being impermeant to said membrane member when said membrane member is intact, said dye indicator serving to provide a visible indication of the existence of a discontinuity in said membrane member.

20. A method of rehydrating a solute to produce a sterile aqueous solution of said solute from non-sterilized fresh water, comprising the steps of:
  separating a supply of non-sterilized fresh water from said solute by a semipermeable membrane member;
  employing a membrane material which is permeable to water and impermeable to said solute and to contaminants such as bacteria, virus and pyrogens, as said membrane member; and
  initiating and accelerating the osmotic transfer of sterile water from said water supply through said membrane member by including a non-toxic, water soluble substance having a high osmotic pressure and being permeant to said membrane member with said solute.

21. The method of claim 20 further comprising the step of adding a dye to said water supply, said dye being impermeant to said membrane member when said member is intact, said dye serving as a failsafe mechanism to visibly indicate the existence of any discontinuity in said membrane member.

22. The method of claim 20 further comprising the step of agitating said water supply, membrane member, solute and osmotic accelerator.

23. The method of claim 22 wherein said solute comprises a polysaccharide and said osmotic accelerator comprises a substance chosen from a group comprising mineral salts and sugars.

24. The method of claim 23 wherein said solution comprises a plasma substitute for intravenous injection, said solute comprises dextran and said osmotic accelerator comprises sodium chloride.

* * * * *

UNITED STATES PATENT AND TRADEMARK OFFICE
CERTIFICATE OF CORRECTION

PATENT NO. : 4,920,105
DATED : April 24, 1990
INVENTOR(S) : Allen Zelman

It is certified that error appears in the above-identified patent and that said Letters Patent is hereby corrected as shown below:

Claim 13, line 20 "mil," should read --milk--.

Claim 15 should read as follows:

--15. The pouch of claim 4 further comprising a sterile solute in said first compartment, said solute comprising a large molecular weight osmotic agent impermeant to said membrane material, and a low molecular weight osmotic accelerator permeant to said membrane member which functions to initiate and accelerate hydrating of the osmotic agent.--

Signed and Sealed this

Twenty-eighth Day of May, 1991

Attest:

HARRY F. MANBECK, JR.

Attesting Officer

Commissioner of Patents and Trademarks